(12) United States Patent
Gippert et al.

(10) Patent No.: US 7,730,885 B2
(45) Date of Patent: Jun. 8, 2010

(54) DEVICE FOR MIXING ANESTHETIC VAPOR WITH ANESTHETIC GAS

(75) Inventors: Karl-Ludwig Gippert, Lübeck (DE); Claus Bunke, Sereetz (DE); Matthias Witt, Bad Schwartau (DE); Rainer Kunz, Lübeck (DE); Jürgen Müller, Lübeck (DE); Sven Heyer, Lübeck (DE); Michael Heidschmidt, Lübeck (DE); Dirk-Stefan Reichert, Lübeck (DE)

(73) Assignee: Dräger Medical AG & Co. KG, Lüeck (DE)

( * ) Notice: Subject to any disclaimer, the term of this patent is extended or adjusted under 35 U.S.C. 154(b) by 1137 days.

(21) Appl. No.: 11/210,197

(22) Filed: Aug. 23, 2005

(65) Prior Publication Data

US 2006/0065269 A1    Mar. 30, 2006

(30) Foreign Application Priority Data

Sep. 25, 2004    (DE) ........................ 10 2004 046 645
Nov. 11, 2004    (DE) ........................ 10 2004 054 416

(51) Int. Cl.
*A61M 15/00*    (2006.01)

(52) U.S. Cl. ............................ 128/203.12; 128/203.14; 128/203.25; 128/203.26; 128/203.27; 128/204.21; 128/204.22

(58) Field of Classification Search ............ 128/203.12, 128/203.14, 203.25, 203.26, 203.27, 204.21, 128/204.22
See application file for complete search history.

(56) References Cited

U.S. PATENT DOCUMENTS

| 3,420,232 A | 1/1969 | Bickford |
| 4,017,566 A * | 4/1977 | Seidel .......................... 261/56 |
| 5,671,729 A | 9/1997 | Moll et al. |

FOREIGN PATENT DOCUMENTS

DE    196 13 754 C1    3/1997

* cited by examiner

*Primary Examiner*—Patricia M Bianco
*Assistant Examiner*—Nihir Patel
(74) *Attorney, Agent, or Firm*—McGlew and Tuttle, P.C.

(57) ABSTRACT

A device for mixing anesthetic vapor with anesthetic gas has a pressure limitation feature achieved in a simple manner. The device has a valve device (11), with which the evaporator is switched on and off. The valve device (11) is equipped with an overpressure release device (22).

8 Claims, 5 Drawing Sheets

DEVICE FOR MIXING ANESTHETIC VAPOR WITH ANESTHETIC GAS

CROSS REFERENCE TO RELATED APPLICATIONS

This application claims the benefit of priority under 35 U.S.C. §119 of German Applications DE 10 2004 046 645.9 of Sep. 25, 2004 and DE 10 2004 054 416.6 filed Nov. 11, 2005, the entire contents of each of which are incorporated herein by reference.

FIELD OF THE INVENTION

The present invention pertains to a device for mixing anesthetic vapor with anesthetic gas.

BACKGROUND OF THE INVENTION

A device of this type has become known from U.S. Pat. No. 3,420,232. Saturated anesthetic vapor from an evaporator chamber is mixed with the anesthetic gas via a dispensing means in the anesthetic vaporizer operating according to the bypass principle in order to set a predetermined concentration of anesthetic in the anesthetic gas. The anesthetic vaporizer is provided with a shut-off valve, which is designed to shut off the gas flow from the evaporator chamber in a first switching position, so that the anesthetic gas reaches a gas outlet from a gas inlet via a bypass line. In a second switching position, the gas flow is released via the evaporator chamber and anesthetic vapor can be mixed with the anesthetic gas with the dispensing device. The shut-off valve comprises a lower part provided with gas ducts, which is part of the evaporator housing, and a rotatably movable upper part, which is fastened thereto in a rotatingly movable manner and has kidney-shaped gas ducts. Depending on the angular position of the upper part, the kidney-shaped gas ducts of the upper part connect corresponding gas ducts in the lower part, so that a gas flow is released via the shut-off valve or the gas ducts in the lower part are closed. The upper part has a carrier pin, which is connected with the setting member for the anesthetic concentration. The shut-off valve is closed in the zero position of the setting member and the anesthetic gas flows via the bypass line directly from the gas inlet to the gas outlet. If the setting member is set to a certain anesthetic concentration starting from the zero position, the shut-off valve opens above the carrier pin and the gas flow from the evaporator chamber is released.

An anesthetic vaporizer, in which it is possible to switch over between a transport position, a zero position and a dispensing position by means of individual valves, which are actuated by the setting member, is known from DE 196 13 754 C1 (corresponding to U.S. Pat. No. 5,671,729). The evaporator chamber is completely closed in the transport position of the setting member, so that neither liquid nor gaseous anesthetic can escape. A ventilating valve, with which the pressure in the evaporator chamber of the anesthetic vaporizer can be released, is opened during the transition from the transport position into the zero position. The ventilating valve is again closed during the transition of the setting member into the dispensing position, so that the anesthetic can be dispensed at the pressure level prevailing during operation.

A certain system pressure must be maintained within the anesthetic tank in case of anesthetics with a low boiling pint in order to prevent the anesthetic from boiling. A pressure control circuit with a differential pressure sensor as well as a dispensing valve is usually used for the dispensing branch in such evaporators. The differential pressure sensor is especially sensitive to high pressure amplitudes and pressure shocks even if these reach the differential pressure diaphragm with an offset in time.

However, an increase in pressure within the anesthetic vaporizer may also be due to external causes, for example, a kinked supply tube for anesthetic gas, which is to be enriched with anesthetic vapor. Such pressure shocks may occur with the anesthetic vaporizer switched on and with the anesthetic vaporizer switched off.

In addition, a pressure build-up, which may damage delicate measuring systems, may occur due to minor leaks at dispensing components within the dispensing device when the anesthetic vaporizer is switched off when the anesthetic gas is sent past the dispensing device directly into the anesthesia apparatus. Even though it would be possible to protect these measuring systems with a separate pressure limiting valve, additional components are necessary for this.

SUMMARY OF THE INVENTION

The basic object of the present invention is to improve a device of the type such that pressure limitation is achieved in a simple manner.

According to the invention, a device is provided with a dispensing device for mixing anesthetic vapor with anesthetic gas and with a valve device. The valve device sends anesthetic gas past the dispensing device from a gas inlet to a gas outlet in a first switching position and establishes a path for the gas via the dispensing device in a second switching position. A lower part of the valve device is provided with gas ducts and an upper part is arranged adjustably above the lower part and is provided with gas ducts wherein gas ducts are provided extending from the lower part via the upper part and back into the lower part in such a way that the first switching position and the second switching position can be established depending on the position of the upper part in relation to the lower part. A clamping device fixes the upper part in relation to the lower part in the form of a pressure limiting means for limiting the pressure in the gas ducts.

The advantage of the present invention is essentially that an overpressure limiting means is integrated within a valve device, with which the dispensing device for anesthetics is either bridged over or released. Provisions are made for this purpose for the upper part of the valve device, with which the switchover function is performed, to be fixed by means of the clamping device in relation to the lower part. The clamping device is dimensioned such that the upper part lifts off from the lower part when a predetermined pressure is exceeded within the gas ducts that extend between the lower part and the upper part. The valve device, with which the dispensing device for anesthetics is either bridged over or released, is usually present at an anesthetic vaporizer. Due to the integration of the clamping device, which fixes the two components of the valve, namely, the upper part and the lower part, in relation to one another, the valve device is provided with an overpressure limiting means. Due to the fact that the valve device is actuated each time the anesthetic vaporizer is switched on and off, the upper part and the lower part are moved in relation to one another during each switching operation, so that the components of the valve are prevented from sticking. By contrast, there is a risk in case of an overpressure limiting valve arranged separately that sticking of the valve body in relation to the valve seat will occur due to aging or anesthetic vapors, so that the overpressure limiting valve may open at an excessively high pressure only. Another advantage of the valve device according to the present invention can be considered to be the fact that not only the dispensing device but also the gas ducts of the anesthetic vaporizer that carry the anesthetic gas are protected from overpressure. An excessively high gas line pressure may develop, for example, due to a kinked gas line, which is arranged downstream of the anesthetic vaporizer.

The valve device can be advantageously designed as a rotary switch or slide switch.

The clamping device is advantageously designed as a clamping device that closes again automatically or remains open. An automatically closing clamping device is preferably a leaf spring or a coil spring or a weight, with which the upper part is pressed against the lower part. A clamping device that remains open may be designed as a stop notch jumping over in case of a limiting force or as a predetermined breaking point in a clamping element.

An exemplary embodiment of the present invention is shown in the drawings and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
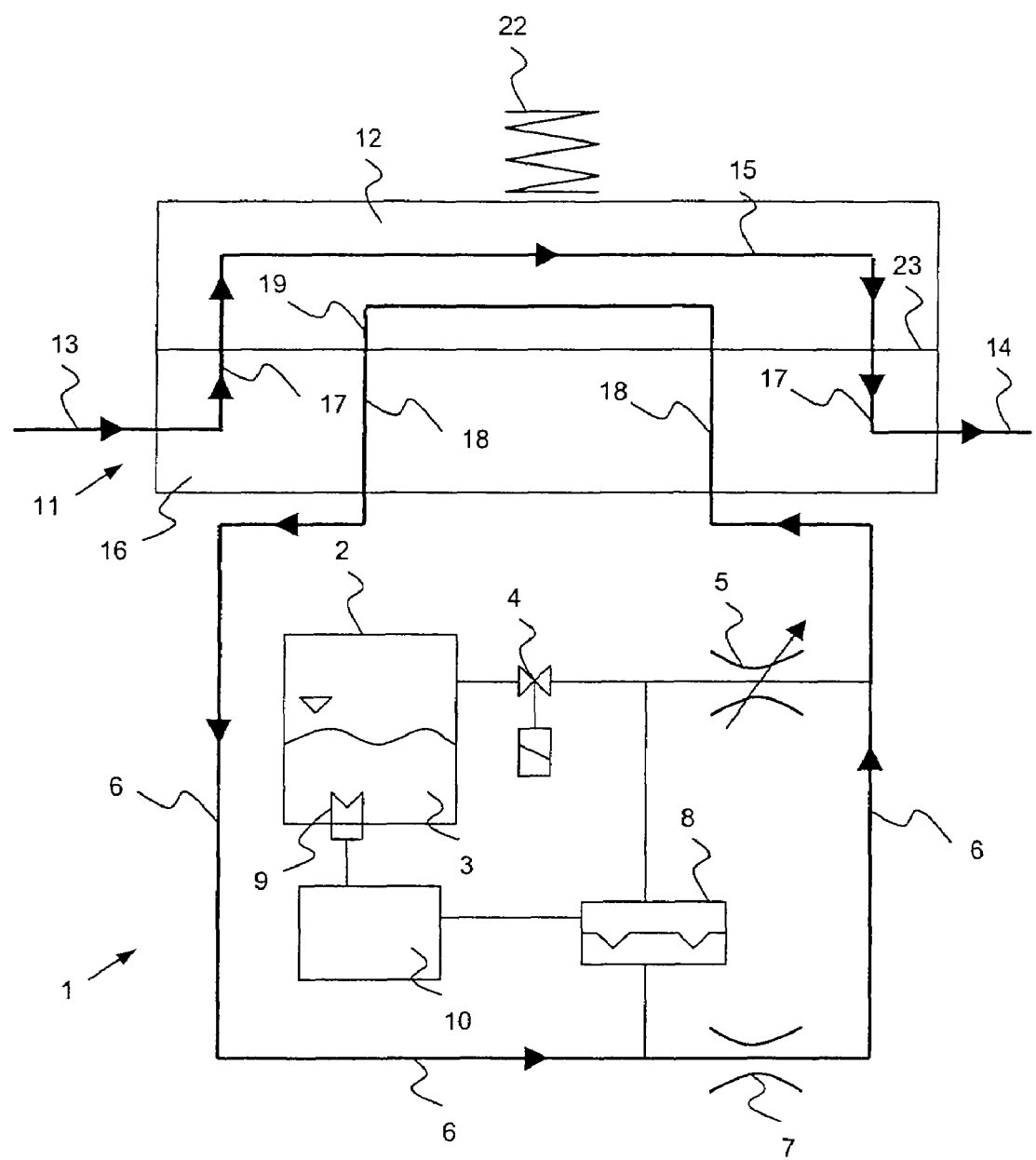
FIG. 1 is schematic view of an anesthetic vaporizer according to the invention in the switched-off state.

Referring to the drawings in particular, FIG. 1 schematically shows an anesthetic vaporizer 1, which contains an anesthetic tank 2 for liquid anesthetic 3, a dispensing valve 4, an adjustable dispensing gap 5, a bypass line 6 with a bypass gap 7, a differential pressure sensor 8, a heater 9 for the anesthetic and an electronic control unit 10. A valve device 11 on the top side of the anesthetic vaporizer 1 has a lower part 16 with a gas inlet 13 and with a gas outlet 14 and gas ducts 17, 18 and an upper part 12 with gas ducts 15, 19. The upper part 12 is fastened against the lower part 16 in the form of a rotary or slide valve, so that individual gas ducts 15, 19 of the upper part 12 are connected to gas ducts 17, 18 of the lower part 16 in predetermined positions of the upper part 12. The upper part 12 is pressed onto the lower part 16 by means of a spring 22.

In the switching position shown in FIG. 1, the gas inlet 13 and the gas outlet 14 are connected to one another directly via the gas ducts 15, 17, and the anesthetic gas is sent past the dispensing device 2, 4, 5, 6, 7. Together with the gas ducts 18, 19, the bypass line 6 now forms a closed circular pipe. The gas ducts 15, 17, 18, 19 cross an interface 23 between the upper part 12 and the lower part 16.

Figure 2:
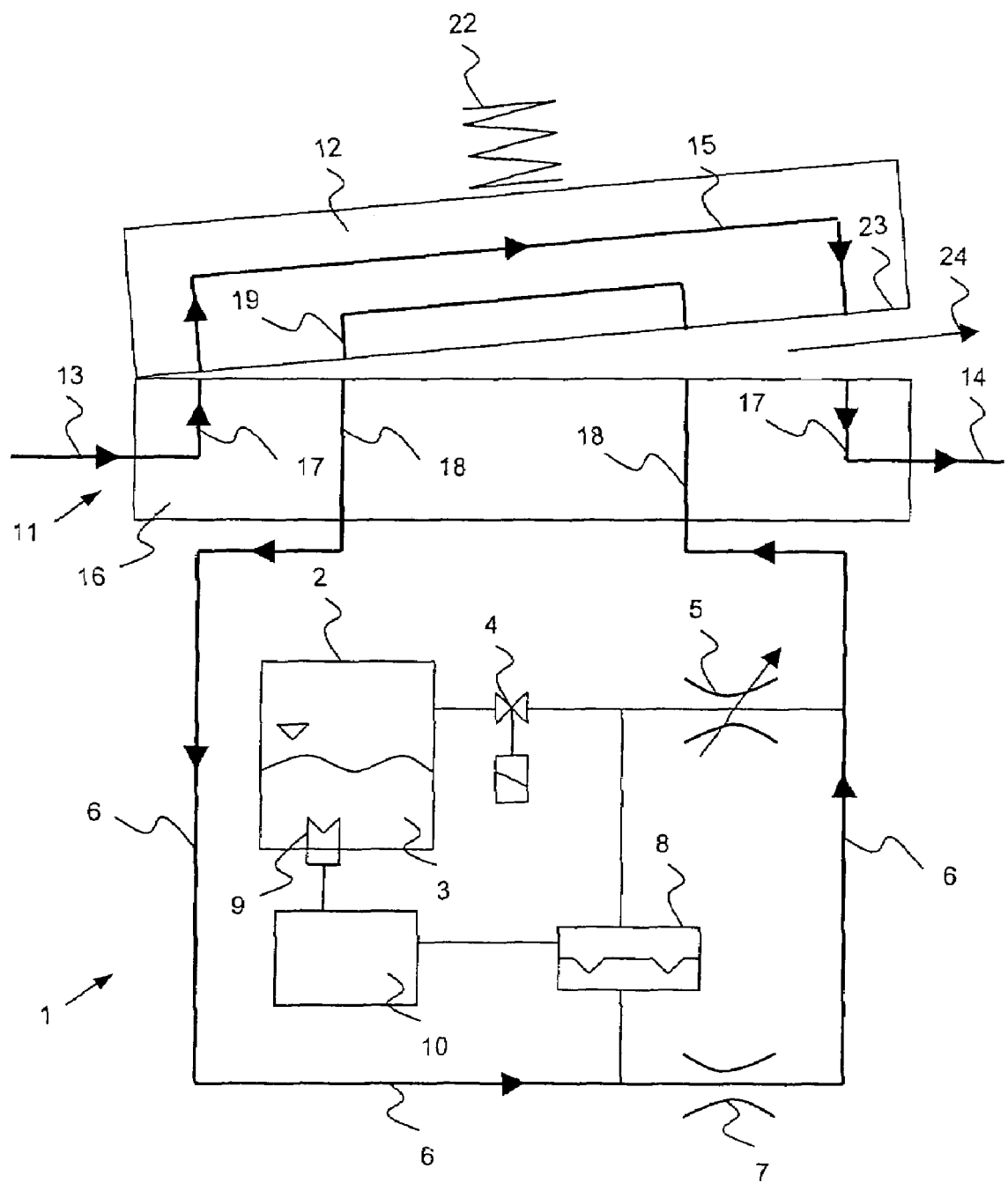
FIG. 2 is schematic view showing the anesthetic vaporizer according to FIG. 1 with the valve device opened.

If an increased pressure or pressure rise occurs within the bypass line 6 or at the differential pressure sensor 8 connected with the bypass line 6, such a pressing force is exerted on the upper part 12 via the gas duct 19 that, as is illustrated in FIG. 2, the upper part 12 lifts off from the lower part 16 and the pressure can drop along arrow 24. Identical components in FIG. 2 are designated by the same reference numbers as in FIG. 1. Since the gas duct 15 is connected to the gas inlet 13 and the gas outlet 14 via the gas ducts 17, the pressure also drops when an increased pressure or pressure rise is present in the gas duct 15.

Figure 3:
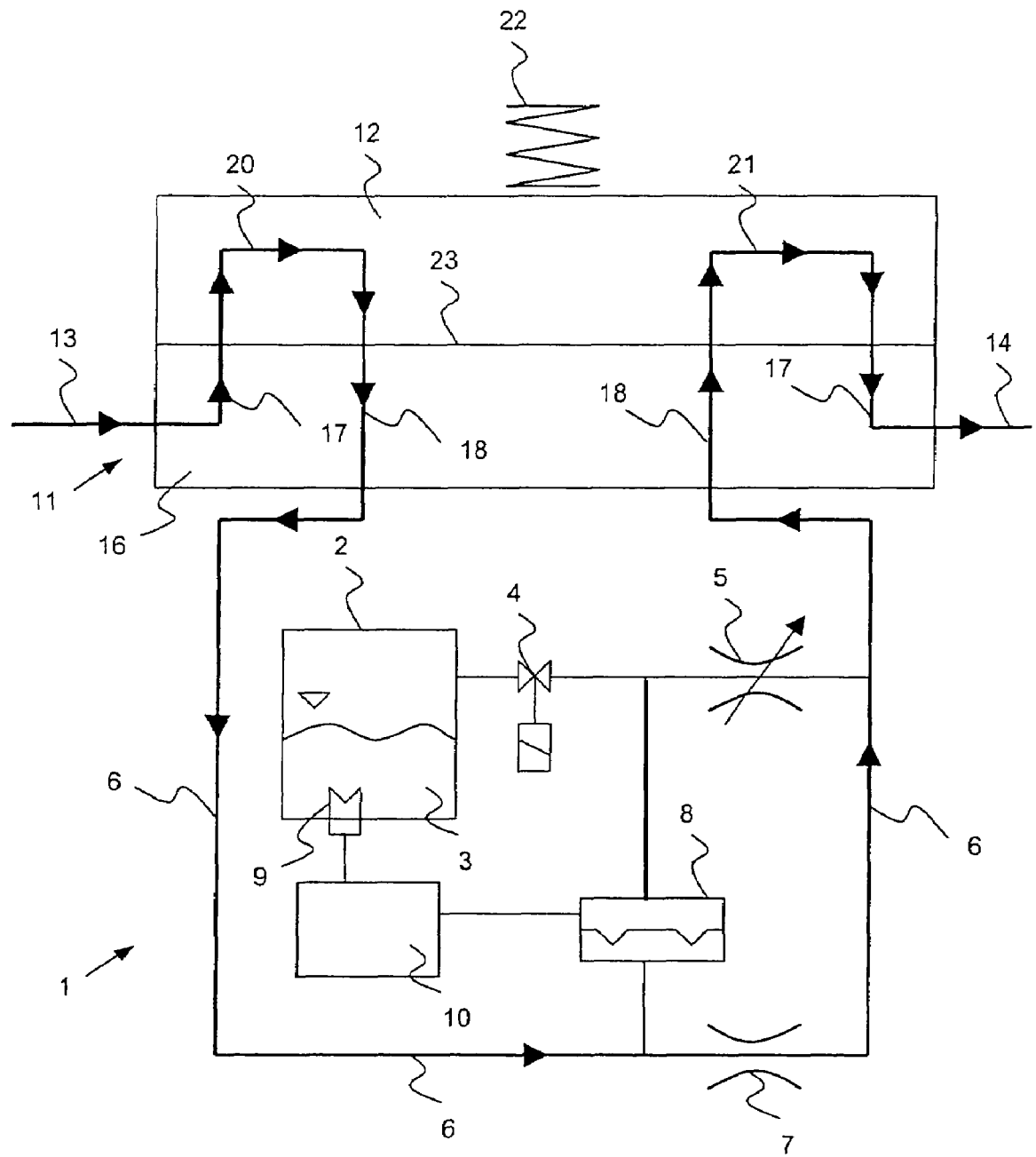
FIG. 3 is schematic view showing an anesthetic vaporizer in the switched-on state.
Figure 4:
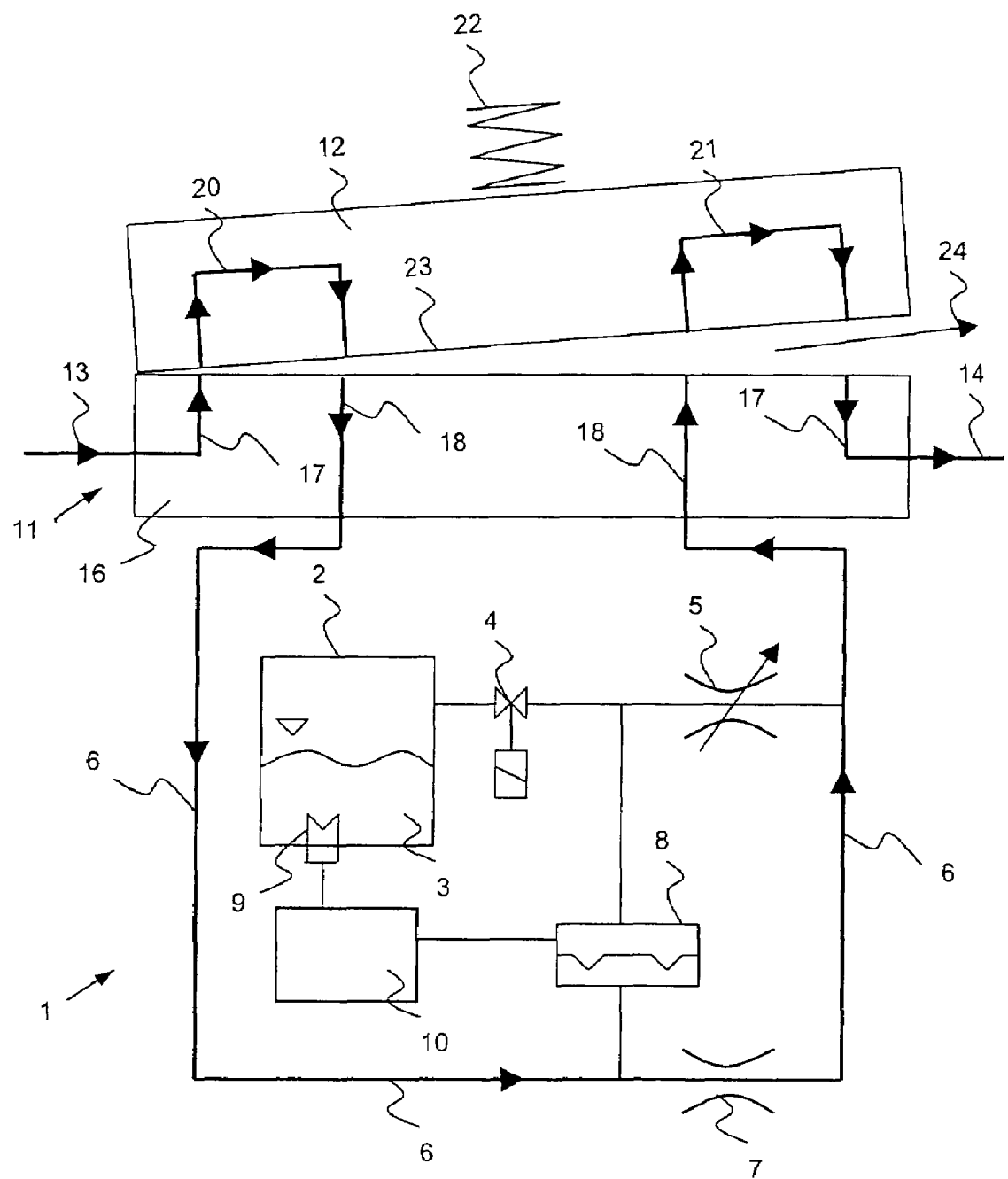
FIG. 4 is schematic view showing the anesthetic vaporizer according to FIG. 3 with the valve device opened.

FIG. 3 illustrates the anesthetic vaporizer 1 in a second switching position in the switched-on state. The gas inlet 13 is connected with the gas outlet 14 here via the gas ducts 17, 18, 20, 21 and the bypass line 6. The gas ducts 20, 21 in the upper part 12 are connected with the corresponding gas ducts 17, 18 of the lower part 16 in this switching position of the valve device 11. If an increased pressure rise occurs within the gas ducts 20, 21, a force will act at the interface 23 between the upper part 12 and the lower part 16, and the upper part 12 is lifted off by this force from the lower part 16, corresponding to FIG. 4, and excess gas can escape along arrow 24. The limiting pressure at which the upper part 12 just lifts off can be set, for example, by selecting the rigidity of the sprig 22. To set the closing force of the spring, an adjusting screw is provided, which is not shown specifically in FIG. 4 and with which the pressing force of the spring 22 can be changed.

Figure 5:
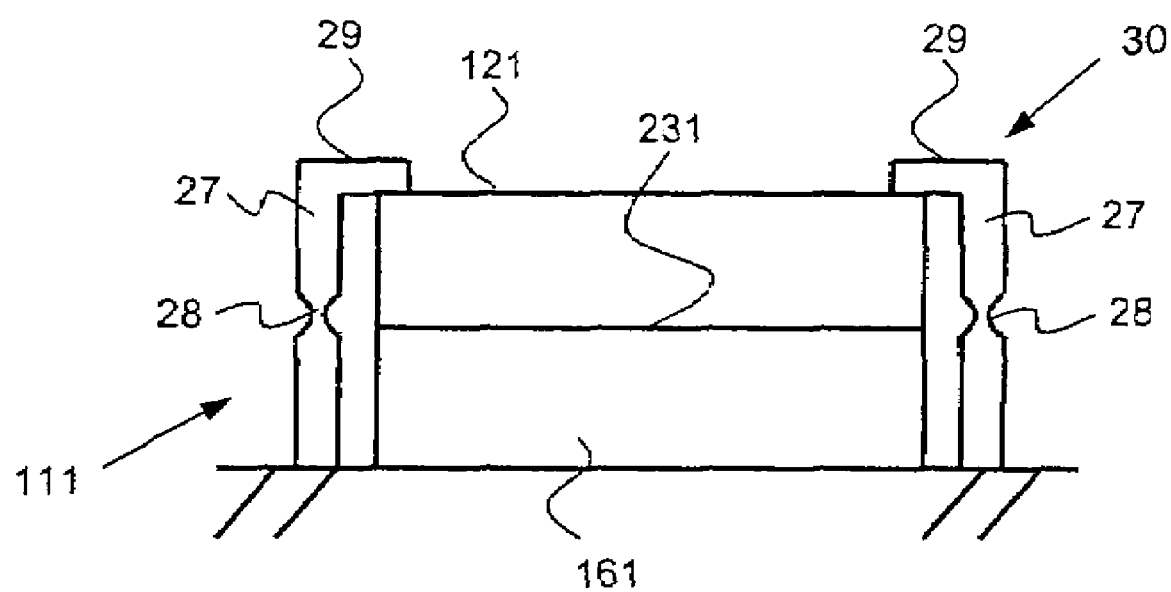
FIG. 5 is schematic view showing an alternative valve device with a clamping device that remains open.

FIG. 5 schematically shows an alternative valve device 111. This valve device is used on the top side of the anesthetic vaporizer 1 in a manner similar to valve device 11. However, the valve device 111 has a clamping device 30 that remains open in the form of two tongues 27 with predetermined breaking points 28. The tongues 27 have hook-shaped clamps 29, with which the upper part 121 is pressed against the lower part 161. When the pressure exceeds a predetermined limit value at the interface 231 between the upper part 121 and the lower part 161, the predetermined breaking points 28 break and the clamps 29 release the upper part 121. An immediate and permanent pressure release takes place.

While specific embodiments of the invention have been shown and described in detail to illustrate the application of the principles of the invention, it will be understood that the invention may be embodied otherwise without departing from such principles.

What is claimed is:

1. A device with a dispensing device for mixing anesthetic vapor with anesthetic gas, the device comprising:

a valve device to send anesthetic gas past the dispensing device from a gas inlet to a gas outlet in a first switching position and to establish a path for the gas via the dispensing device in a second switching position and including a lower part provided with gas ducts at the valve device and with an upper part arranged adjustably above said lower part, said upper part including gas ducts with upper part and lower part gas ducts defining ducts extending from the lower part via the upper part and back into the lower part in such a way that the first switching position and the second switching position can be established depending on the position of the upper part in relation to the lower part; and a clamping device fixing the upper part in relation to the lower part in the form of a pressure limiting means for limiting the pressure in the gas ducts, said clamping device opening for gas release for pressure limiting and automatically closing again.

2. A device in accordance with claim 1, wherein the lower part in combination with the upper part form a rotary switch or slide switch.

3. A device in accordance with claim 1, wherein the clamping device includes a spring.

4. A device in accordance with claim 3, wherein the clamping device includes an adjusting screw wherein the pretensioning force of the spring can be set with the adjusting screw.

5. An anesthetic vapor with anesthetic gas mixing device, comprising:
 a dispensing device for mixing anesthetic vapor with anesthetic gas, the device comprising:
 a valve device for controlling gas flow to the dispensing device including a first switching position for gas flow from a gas inlet to a gas outlet and a second switching position to establish a path for the gas via the dispensing device in the second switching position, the valve device including a lower part provided with gas ducts and an upper part arranged adjustably above said lower part, said upper part including gas ducts with upper part and lower part gas ducts defining ducts extending from the lower part via the upper part and back into the lower part in such a way that the first switching position and the second switching position can be established depending on the position of the upper part in relation to the lower part; and
 an overpressure release means for holding the upper part in relation to the lower part up to a pressure level prevailing in the ducts extending from the lower part and allowing venting of the ducts extending from the lower part via the upper part upon the pressure level prevailing in the ducts extending from the lower part exceeding the pressure level, the over pressure release means opening the upper part relative to the lower part for gas release for pressure limiting and automatically closing the upper part relative to the lower part again.

6. A device in accordance with claim 5, wherein the lower part in combination with the upper part form a rotary switch or slide switch and the pressure device allows movement of the upper part upwardly relative to the lower part to limit the pressure up prevailing in the ducts extending from the lower part.

7. A device in accordance with claim 5, wherein the over pressure release means includes a spring.

8. A device in accordance with claim 7, wherein the over pressure release means includes an adjusting screw wherein the pretensioning force of the spring can be set with the adjusting screw.

* * * * *